US008692070B2

(12) United States Patent
McLaren et al.

(10) Patent No.: US 8,692,070 B2
(45) Date of Patent: Apr. 8, 2014

(54) PLANTS WITH IMPROVED NITROGEN UTILIZATION AND STRESS TOLERANCE

(75) Inventors: James McLaren, Chesterfield, MO (US); Nicholas Duck, Research Triangle Park, NC (US); Brian Vande Berg, Research Triangle Park, NC (US); Philip Hammer, Research Triangle Park, NC (US); Laura Schouten, Research Triangle Park, NC (US)

(73) Assignee: Iowa Corn Promotion Board, Johnston, IA (US)

( * ) Notice: Subject to any disclaimer, the term of this patent is extended or adjusted under 35 U.S.C. 154(b) by 272 days.

(21) Appl. No.: 12/916,854

(22) Filed: Nov. 1, 2010

(65) Prior Publication Data

US 2011/0252503 A1 Oct. 13, 2011

Related U.S. Application Data

(60) Provisional application No. 61/258,075, filed on Nov. 4, 2009.

(51) Int. Cl.
| | |
|---|---|
| C12N 15/82 | (2006.01) |
| C12N 15/87 | (2006.01) |
| A01H 5/00 | (2006.01) |
| A01H 5/10 | (2006.01) |
| C12N 1/21 | (2006.01) |
| C12N 15/00 | (2006.01) |
| C12N 15/29 | (2006.01) |
| C12N 15/54 | (2006.01) |
| C07H 21/04 | (2006.01) |

(52) U.S. Cl.
USPC ............... 800/290; 800/320.1; 435/252.3; 435/320.1; 435/194; 536/23.6

(58) Field of Classification Search
None
See application file for complete search history.

(56) References Cited

U.S. PATENT DOCUMENTS

| 7,569,389 B2 | 8/2009 | Feldmann et al. | |
|---|---|---|---|
| 2004/0214272 A1 | 10/2004 | La Rosa et al. | |
| 2005/0155100 A1* | 7/2005 | Blau et al. | 800/278 |
| 2006/0150283 A1 | 7/2006 | Alexandrov et al. | |
| 2011/0179519 A1 | 7/2011 | Coruzzi et al. | |

FOREIGN PATENT DOCUMENTS

| EP | 1801206 A1 | 6/2007 |
|---|---|---|
| EP | 1990416 A1 | 11/2008 |
| JP | 2008/513004 A | 5/2008 |
| WO | WO0004168 A1 | 1/2000 |
| WO | 2008/051608 A2 | 5/2008 |

OTHER PUBLICATIONS

Parsot et al 1993 Genbank, http://www.ncbi.nlm.nih.gov/nuccore/m21446.*
Slocum 2005 Plant Physiology and Biochemistry 43: p. 729-745.*
McAllister et al 2012 Plant Biotechnology Journal, pp. 1-15.*
Ming-Hsiun Hsieh, Hon-Ming Lam, Frank J. Van De Loo, and Gloria Coruzzi (1998). A PII-like protein in Arabidopsis:Putative role in nitrogene sensing. Proc. Natl. Acad. Sci. 95, 13965-13970.
Takashi Osanai and Kan Tanaka. (2007). Keeping in Touch with PII: PII-Interacting Proteins in Unicellular Cyanobacteria. Plant and Cell Physiology 48(7):908-914.
Llacer, et al., Arginine and nitrogen storage, Curr Opinion Struct Biol (Dec. 2008) vol. 18, No. 6, p. 673-681, p. 673, col. 2, para 3.
Gil et al. N-Acetyl-L-glutamate kinase from Escherichia coli: cloning of the gene, purification and crystallization of the recombinant enzyme and preliminary X-ray analysis of the free andligand-bound forms. Acta Crystallogr D Biol Crystallogr. Jul. 1999;55(Pt 7): 1350-2. (abstract only).
Fernandez-Murga, et al., Arginine Bisynthesis in Thermotoga maritima: Characterization of the Arginine-Sensitive N-Acetyl-L-Glutamate Kinase, J Bacteriol (Sep. 2004) vol. 186, No. 18, p. 6142-6149.
Slocum, Genes, enzymes and regulation of arginine biosynthesis in plants, Plant Physiol and Bioch (Aug. 2005) vol. 43, No. 8, p. 729-745.
Burillo et al. "Interactions between the Nitrogen Signal Transduction Protein PII and N-Acetyl Glutamate Kinase in Organisms That Perform Oxygenic Photosynthesis" J. Bact. 2004 v 186, n 11 p. 3346-3354. entire document.
Llacer et al. The crystal structure of the complex of PII and acetyglutamate kinase reveals how PII controls the storage of nitrogen as arginine. PNAS, Nov. 6, 2007, vol. 104, No. 45, p. 17644-17649. entire document.
Heinrich et al. "The Synechococcus elongatus PII signal transduction protein controls arginine syntheses by complex formation with N-acetyl-L-glutamate kinase" Molecular Microbiology (2004) 52 (5), 1303-1314. entire document.
Ramon-Maiques et al. "Structure of Acetylglutamate Kinase, a Key Enzyme for Arginine Biosyntheses and a Prototype for the Amino Acid Kinase Enzyme Family, during Catalysis" Structure, Mar. 2002, vol. 10, 329-342. entire document.

(Continued)

Primary Examiner — David T Fox
Assistant Examiner — Matthew Keogh
(74) Attorney, Agent, or Firm — Davis, Brown, Koehn, Shors & Roberts, P.C.; Kent A. Herink

(57) ABSTRACT

The present invention relates to transgenic plants that have increased nitrogen use efficiency, stress tolerance, and/or alleviating a limitation such that yield is increased, or a combination of these and that have been transformed using a novel vector construct including a synthetic N-acetyl glutamate kinase (NAGK) gene that modulates nitrogen use in plants. The invention also includes the overexpression and enzymatic characterization of an arginine-insensitive NAGK isolated from a bacterial strain that improves stress tolerance and nitrogen uptake, metabolism or both. In various embodiments, the vector construct includes one or more nucleic acid sequences including SEQ ID NO: 1. The invention also relates to isolated vectors for transforming plants and to antibodies used for detecting transformed plants. The invention also relates to methods of expressing in plants the nucleic acid molecules corresponding to the nucleic acid sequences that modulate nitrogen use in plants or are modulated by nitrogen conditions.

23 Claims, 3 Drawing Sheets

(56) References Cited

OTHER PUBLICATIONS

Bourrellier, A.B.F., Ferrario-Mery, S., Vidal, J. Hodges, M. (2009). Metabolite regulation of the interaction between *Arabidopsis thaliana* PII and N-aetyl-L-glutamate kinase. Biochem. Biophys. Res. Commun. 387: 700-704.

Denes, G. (1970). N-Acetylglutamate-5-phosphotransferase (*Chlamydomanas reinhardti*). Methods in Enz. 17:269-272.

Fernandez-Murga, Fil-Ortiz, F., Llacer, J.L., Rubio, V. (2004). Arginine biosynthesis in *Thermotoga maritima:* characterization of the arginine-sensitive N-acetyl-L-glutamate kinase. J. Bact. 186: 6142-6149.

Llacer, J.L., Fita, I., Rubio V. (2008). Arginine and nitrogen storgage. Curr. Opinion in Struct. Biol. 18: 673-681.

Lohmeier-Vogel, E.M., Loukanina, N., Ferrar, T.S. Moorhead, G.B. G., Thorpe, T.A. (2005). N-acetyl glutamate kindase form *Daucus carota* suspension cultures: embryongenic expression profile, purification and characterization. Plant Phys. and Biochem. 43: 854-861.

\* cited by examiner

SEQUENCE LISTING

<160> NUMBER OF SEQ ID NOS: 3

<210> SEQ ID NO 1
<211> LENGTH: 836
<212> TYPE: DNA
<213> ORGANISM: Zea mays

<400> SEQUENCE: 1

```
atgctgcatg aggtgatggt gatcaagtgc ggcggcagca tgctggagca gctgccggag      60
agcttctaca acaagctggc gacgctgcaa gcagaaggaa gaagcatcgt cattgttcat     120
ggaggagggc cggccatcaa ccagatgctg gagcagctga agattgagcc aaccttctca     180
aatgggctga gggtgacaga tgagccaaca atgcaagctg tggagatggt gctctcaggg     240
cccatcaaca agctggtggt gaggaagctg ctgcacgccg cggcaaggc atggggcctc     300 agcggcgtgg atggaagcct gctgcaagct gttgagaaga ctcaaggcct cggcctggtg     360
ggcagcatca ccgtggtgga tcaagcgccg ctccagctgc tgctgagcaa tggctacatc     420
ccggtggtgt ctcccatcgc cgtctcagaa gatggaagaa caagatacaa ctgcaacgcc     480
gacaccgtcg ccggcgccat tgcttcagct ctcggcgcca agcagctgct gatgctcact     540
gatgttcctg gcatctgggc agaaaatgag ctgggagaga agcagctgct gccgacggtg     600
acaacagaag atattcagct gatgatgaag aaccagatca tcaccggcgg catgatcccc     660
aaggtgcaag cggcgctgga tgctctagct caaggagttc aagaagtggt gatctgcaaa     720
ggagaagctg agacgctgga cggcgtggtg aagggcatgg ccgtcggcac ctccatctcc     780
gccgagatga gcagaggaca agattctcaa gccttcatca gcaacaaggt gtgagg       836
```

<210> SEQ ID NO 2
<211> LENGTH: 277
<212> TYPE: PRT
<213> ORGANISM: Zea mays

<400> SEQUENCE: 2

```
Met Leu His Glu Val Met Val Ile Lys Cys Gly Gly Ser Met Leu Glu
1               5                   10                  15

Gln Leu Pro Glu Ser Phe Tyr Asn Lys Leu Ala Thr Leu Gln Ala Glu
            20                  25                  30

Gly Arg Ser Ile Val Ile Val His Gly Gly Pro Ala Ile Asn Gln
        35                  40                  45

Met Leu Glu Gln Leu Lys Ile Glu Pro Thr Phe Ser Asn Gly Leu Arg
50                  55                  60

Val Thr Asp Glu Pro Thr Met Gln Ala Val Glu Met Val Leu Ser Gly
65                  70                  75                  80

Pro Ile Asn Lys Leu Val Val Arg Lys Leu Leu His Ala Gly Gly Lys
                85                  90                  95

Ala Trp Gly Leu Ser Gly Val Asp Gly Ser Leu Leu Gln Ala Val Glu
            100                 105                 110

Lys Thr Gln Gly Leu Gly Leu Val Gly Ser Ile Thr Val Val Asp Gln
            115                 120                 125

Ala Pro Leu Gln Leu Leu Leu Ser Asn Gly Tyr Ile Pro Val Val Ser
130                 135                 140

Pro Ile Ala Val Ser Glu Asp Gly Arg Thr Arg Tyr Asn Cys Asn Ala
145                 150                 155                 160

Asp Thr Val Ala Gly Ala Ile Ala Ser Ala Leu Gly Ala Lys Gln Leu
                165                 170                 175

Leu Met Leu Thr Asp Val Pro Gly Ile Trp Ala Glu Asn Glu Leu Gly
            180                 185                 190

Glu Lys Gln Leu Leu Pro Thr Val Thr Thr Glu Asp Ile Gln Leu Met
            195                 200                 205

Met Lys Asn Gln Ile Ile Thr Gly Gly Met Ile Pro Lys Val Gln Ala
210                 215                 220

Ala Leu Asp Ala Leu Ala Gln Gly Val Gln Glu Val Val Ile Cys Lys
225                 230                 235                 240

Gly Glu Ala Glu Thr Leu Asp Gly Val Val Lys Gly Met Ala Val Gly
                245                 250                 255

Thr Ser Ile Ser Ala Glu Met Ser Arg Gly Gln Asp Ser Gln Ala Phe
            260                 265                 270

Ile Ser Asn Lys Val
            275
```

<210> SEQ ID NO 3
<211> LENGTH: 225
<212> TYPE: DNA
<213> ORGANISM: Zea mays

<400> SEQUENCE: 3

```
atgcagctgc tcaaccagcg gcaggcgctg cggctgggaa gaagctccgc cagcaagaac    60
cagcaggtgg cgccgctggc atcaaggccg gcaagcagcc tctccgtctc cgcctcctcc   120
gtggcgccgg cgccggcctg ctcggcgccg gccggcgccg gccgccgcgc cgtggtggtg   180
cgcgcctccg ccaccaagga gaaggtggag gagctcacca tccag                   225
```

PLANTS WITH IMPROVED NITROGEN UTILIZATION AND STRESS TOLERANCE

This application claims priority to U.S. Patent Application Ser. No. 61/258,075 filed Nov. 4, 2009.

FIELD OF THE INVENTION

The invention relates generally to plants with improved nitrogen utilization and stress tolerance, more specifically, to heterologous expression of an arginine-insensitive N-acetyl glutamate kinase (NAGK) enzyme in plants, including the overexpression and enzymatic characterization of an arginine-insensitive NAGK isolated from a bacterial strain that improves stress tolerance and nitrogen uptake, metabolism or both.

BACKGROUND OF THE INVENTION

Plants require nitrogen during their vegetative and reproductive growth phases. Nitrogen is made available to the plant through soil mineralization, the application of nitrogen fertilizer, or both. It has been estimated, however, that between 50 and 70 percent of nitrogen applied to crops is lost from the plant-soil system [Peoples, M. B. et al., "Minimizing Gaseous Losses of Nitrogen," In *Nitrogen Fertilizer in the Environment* (Bacon, P. E., ed.) Marcel Dekker, pp. 565-606 (1995)]. Nitrogen is one of the most expensive plant nutrients to supply, nitrogen fertilizer is not always available at a reasonable cost, and excessive application of nitrogen fertilizer can result in environmental challenges. Corn is an example of an agronomically important plant that often requires nitrogen fertilizers to perform at its genetic potential.

In plant cells, NAGK (N-Acetyl Glutamate Kinase) carries out the second step in a biosynthetic pathway that leads to the production of arginine. Importantly, several plant and bacterial NAGK enzymes are known to be inhibited by high concentrations of arginine (Bourrellier, 2009; Llacer, 2008; Lohmeier-Vogel, 2005; Fernandez-Murga, 2004), which suggests that NAGK plays a role in arginine regulation in plants. Additionally, it has been demonstrated that the plant P-II protein can mitigate the arginine-based inhibition of NAGK. P-II is known to play a key role in regulation of carbon and nitrogen flow in plants (Bourrellier, 2009; Llacer, 2008).

One strategy to upregulate the arginine biosynthetic pathway in plants is to reduce or eliminate the inhibition of NAGK by arginine. This can be achieved by heterologous expression of an arginine-insensitive NAGK enzyme in plants. Here, we describe the overexpression and enzymatic characterization of an arginine-insensitive NAGK isolated from a bacterial strain.

SUMMARY OF THE INVENTION

The present invention relates to transgenic plants that have increased nitrogen use efficiency, stress tolerance, or both, that have been transformed using a novel vector construct including an arginine-insensitive NAGK nucleic acid sequence that modulates nitrogen use in plants. A variety of NAGK nucleic acid sequences were identified in a library of bacterial strains some of which were novel NAGK genes. An alternative method of identifying NAGK genes for use with the present invention are the several bacterial and plant genomic sequencing projects that have been archived in public databases from which sequences that encode NAGK enzymes with robust activity could be selected. The invention also relates to isolated vectors for transforming plants and to antibodies for detecting expression of the nucleotide sequence of interest in the transformed plants. The invention also relates to methods of expressing in plants the nucleic acid molecules corresponding to the nucleic acid sequences that modulate nitrogen use in plants.

Specifically, vectors for transforming plants and bacterial cells have been constructed using the nucleotide sequence SEQ ID NO: 1, as well as variants, fragments, and complements thereof. These vectors include a 5' DNA promoter sequence and a 3' terminator sequence, wherein the nucleic acid sequence, the DNA promoter sequence, and the terminator sequence are operatively coupled to permit transcription of the nucleotide sequence. In some embodiments, the promoter sequence may be a constitutive plant promoter or a tissue specific promoter.

The invention also includes polyclonal antibodies, comprising polyclonal antibodies to a polypeptide encoded by nucleotide sequence SEQ ID NO: 1.

The invention also includes plants transformed with a nucleotide sequence selected SEQ ID NO: 1, as well as variants and fragments thereof. The plant is selected from the group consisting of corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, grasses (such as turf grasses, forage grasses, or pasture grasses), ornamentals, trees (such as fruit trees, nut trees, pulp trees, oil palms) and conifers. The invention also includes a component part of such plants, plant seed produced from such plants, and a plant seed transformed with a vector construct of the present invention.

The invention also includes a host cell transformed with a nucleotide sequence SEQ ID NO: 1. The host cell may be a bacterial cell or a plant cell.

The invention also includes a method of expressing a nucleic acid molecule that modulates nitrogen in a plant, said method comprising the steps of providing a transgenic plant or plant seed transformed with a vector construct according to the present invention, and growing the transgenic plant or a plant grown from the transgenic plant seed under conditions effective to express the nucleic acid molecule in said transgenic plant or said plant grown from the transgenic plant seed. Growing of the transgenic plant is effective in increasing nitrogen uptake of said transgenic plant or said plant grown from the transgenic plant seed, and/or in increasing efficiency of nitrogen utilization of said transgenic plant or said plant grown from the transgenic plant seed, and/or alleviating a limitation such that yield is increased in said transgenic plant or said plant grown from the transgenic plant seed. The invention also includes the foregoing methods wherein a transgenic plant is provided or a transgenic seed is provided. The invention also includes the foregoing method wherein the plant is selected from the group consisting of corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, grasses (such as turf grasses, forage grasses, or pasture grasses), ornamentals, trees (such as fruit trees, nut trees, pulp trees, oil palms) and conifers.

The invention also includes a method of improving the stress tolerance of a plant by expressing a nucleic acid molecule modulated by nitrogen in a plant, said method comprising the steps of providing a transgenic plant or plant seed transformed with a vector construct according to the present invention and growing the transgenic plant or a plant grown from the transgenic plant seed under conditions effective to express the nucleic acid molecule in said transgenic plant or said plant grown from the transgenic plant seed.

The invention also includes a method of altering the morphology of a plant by expressing a nucleic acid molecule modulated by nitrogen in a plant, said method comprising the steps of providing a transgenic plant or plant seed transformed with a vector construct according to the present invention and growing the transgenic plant or a plant grown from the transgenic plant seed under conditions effective to express the nucleic acid molecule in said transgenic plant or said plant grown from the transgenic plant seed.

The invention also includes a vector construct, comprising a nucleotide sequence encoding the NAGK amino acid sequence SEQ ID NO: 2, a 5' DNA promoter sequence, and a 3' terminator sequence, wherein the nucleotide sequence, the DNA promoter sequence, and the terminator sequence are operatively coupled to permit transcription of the nucleotide sequence.

The invention also includes a vector construct comprising a nucleotide sequence that modulates nitrogen in a plant, wherein said nucleotide sequence is of SEQ ID NO: 1; a nucleotide sequence having at least 85% sequence identity to the nucleotide sequence of SEQ ID NO: 1, wherein said nucleotide sequence modulates nitrogen in a plant; a nucleotide sequence encoding the NAGK amino acid sequence SEQ ID NO: 2; and, a nucleotide sequence encoding an amino acid sequence having at least 85% sequence identity to the amino acid sequence of SEQ ID NO: 2, wherein said nucleotide sequence modulates nitrogen in a plant, wherein said construct further comprises a 5' DNA promoter sequence and a 3' terminator sequence, wherein the nucleotide sequence, the DNA promoter sequence, and the terminator sequence are operatively coupled to permit transcription of the nucleotide sequence.

DETAILED DESCRIPTION OF PREFERRED EMBODIMENTS

Figure 1:
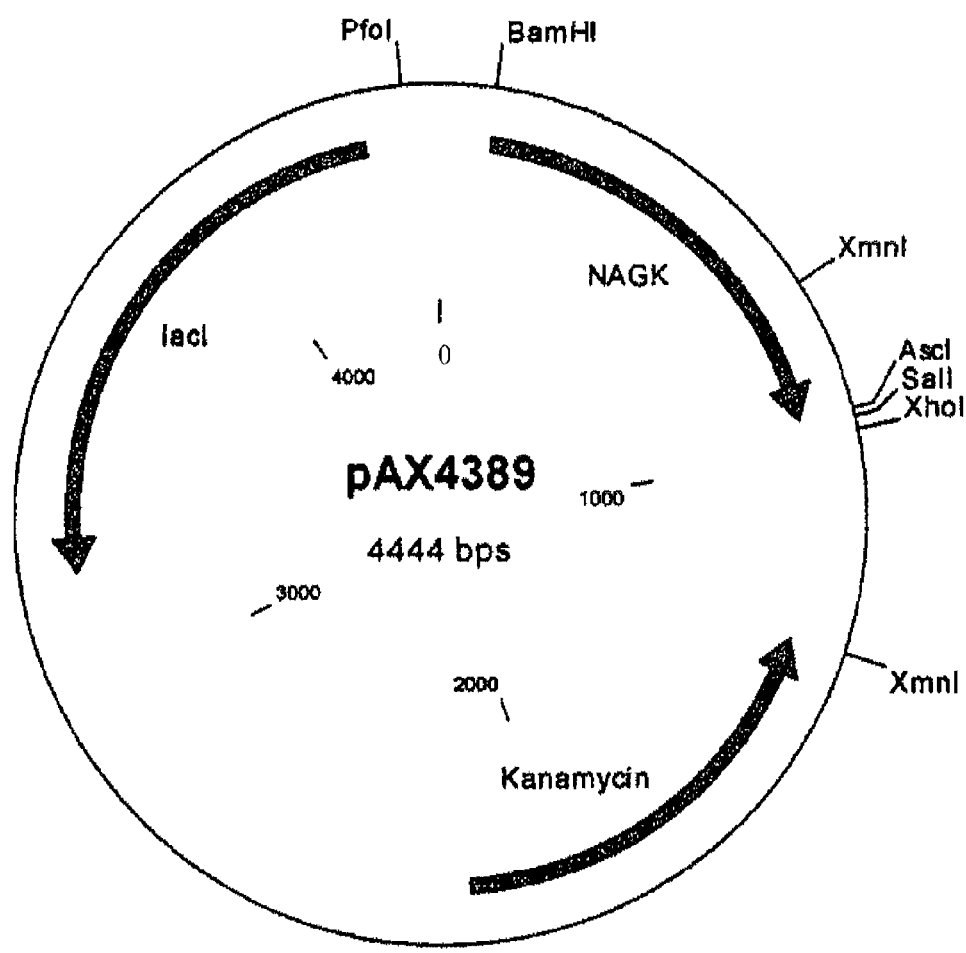
FIG. 1 is a vector map for pAX4389.
Figure 2:
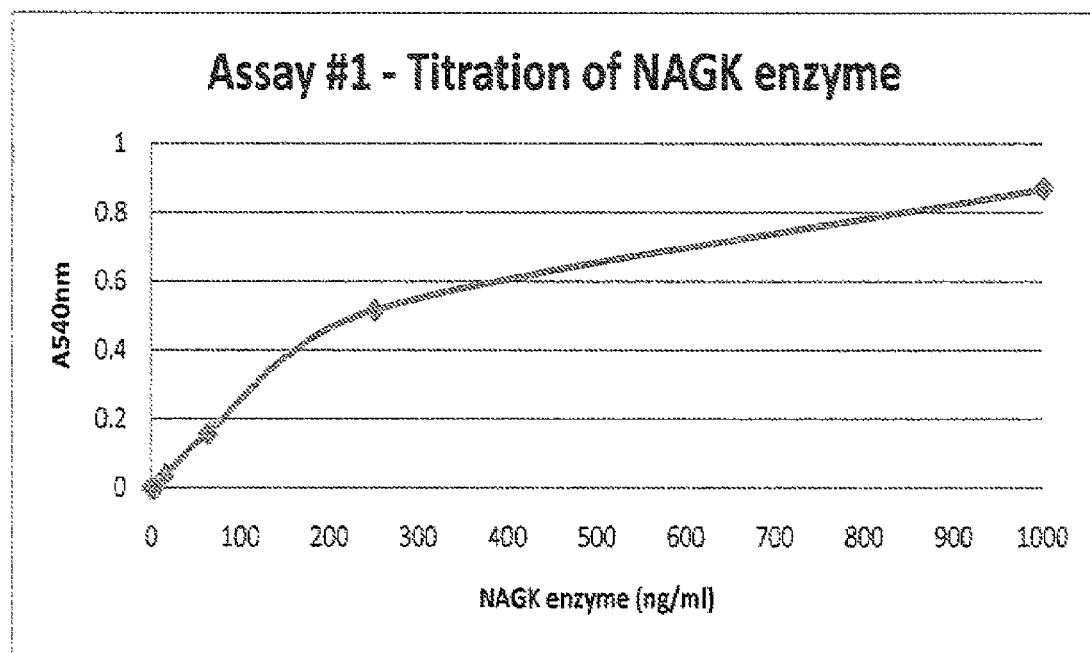
FIG. 2 is a graph of an NAGK in vitro enzyme assay; titration with enzyme. Addition of NAGK enzyme to substrate (NAG) leads to the formation of product in an enzyme-dependent manner.

The development of plant varieties that use nitrogen more efficiently will reduce the need for excessive inputs of nitrogen, save production costs for farmers, benefit farmers in developing countries who do not have access to fertilizer inputs, and reduce environmental contamination associated with the application of excessive nitrogen fertilizers. One approach that has been used in the development of plant varieties with improved nitrogen utilization relies on conventional plant breeding techniques. However, such approaches have had variable success due to lack of specification in the genetic recombination.

There is a need to develop plant cultivars that absorb and use nitrogen more efficiently. Plant scientists have adopted the shorthand term nitrogen use efficiency (NUE), and a variety of methods of measuring and evaluating NUE have been developed [Craswell, E. T. and Godwin, D. C. (1984) The efficiency of nitrogen fertilizers applied to cereals grown in different climates. In Advances in Plant Nutrition (Vol. 1) (Tinker, P. B. and Lauchli, A., eds), pp. 1-55, Praeger Publishers; Steenbjerg, F. and Jakobsen, S. T. (1963) Plant nutrition and yield curves. Soil Sci. 95, 69-90; Siddiqi, M. Y. and Glass, D. M. (1981) Utilization index: a modified approach to the estimation and comparison of nutrient utilization efficiency in plants. J. Plant Nutr. 4, 289-302; Moll, R. H. et al. (1982) Analysis and interpretation of factors which contribute to efficiency of nitrogen utilization. Agron. J. 74, 562-564]. There are differences in the specific definitions, and context of use. For example, some definitions are based on total biomass while others are based on the weight of grain yielded. Another set of definitions uses the efficiency of extracting nitrogen from the soil. The efficiency with which applied nitrogen is used to improve grain yield may be measured by agronomic efficiency (AE), the product of physiological efficiency and utilization efficiency, or NUEg which is the product of uptake efficiency and utilization efficiency. Other definitions take physiological factors into account.

As used in this specification, the term nitrogen use efficiency, or NUE, is defined to include a measurable change in any of the main nitrogen metabolic pool sizes in the assimilation pathways (for example, may include a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the plant is shown to provide the same or elevated biomass or harvestable yield at lower nitrogen fertilization levels, or where the plant is shown to provide elevated biomass or harvestable yields at the same nitrogen fertilization levels when compared to a plant that has not been transformed with a nitrogen-modulating nucleic acid construct of the invention. A "measurable change" can include an increase or a decrease in the amount of any component ("metabolic pool") of the nitrogen assimilation pathway. A change can include either a decrease or an increase in one or more metabolic pools in the pathway, or a decrease in one or more pools with a concomitant increase in one or more other pool(s), such as when one intermediate in the nitrogen assimilation pathway is being utilized for the purpose of generating another intermediate or product of the pathway. For example, in the conversion of glutamate to glutamine, the level of glutamate may decrease while the level of glutamine may increase. Thus, while not being bound by any particular theory or mechanism, any change in one or more of these pools indicates that nitrogen is being utilized more efficiently by the plant.

An increase in nitrogen utilization efficiency can be associated with about a 5%, about a 10%, 15%, 20%, 30%, 40%, 50%, 60%, 70%, 80%, 90%, 100%, 125%, 150%, about a 200% or greater measurable change in any of the main nitrogen metabolic pool sizes in the assimilation pathway. In one embodiment, the transgenic plants of the invention have an increased nitrogen uptake from the environment when compared to a plant that does not contain a nitrogen-modulating sequence of the invention. By "nitrogen modulating sequence" it is intended to mean a nucleotide or amino acid sequence that modulates NUE, by way of non-limiting example: either by generating an enzyme that impacts NUE, or by generating a protein that interacts with the components involved in NUE, or by generating a protein that impacts the internal homeostatic signal cascade regulating NUE, or by a combination of these mechanisms. The present invention further provides a method of improving stress tolerance in a plant by expressing one or more nitrogen-modulating nucleotide sequences within the plant. In one embodiment, the nitrogen-modulating nucleotide sequence is SEQ ID NO: 1, or variants and fragments thereof. In another embodiment, the nitrogen-modulating nucleotide sequence is a nucleotide sequence that encodes SEQ ID NO: 2, or variants and fragments thereof.

As used herein, the term "stress" or "stress condition" refers to the exposure of a plant, plant cell, or the like, to a physical, environmental, biological or chemical agent or condition that has an adverse effect on metabolism, growth, development, propagation and/or survival of the plant (collectively "growth"). A stress can be imposed on a plant due, for example, to an environmental factor such as water (e.g., flooding, drought, dehydration), anaerobic conditions (e.g., a low level of oxygen), abnormal osmotic conditions, salinity or temperature (e.g., hot/heat, cold, freezing, frost), a deficiency of nutrients such as nitrogen, phosphate, potassium, sulfur, micronutrient, or exposure to pollutants, or by a hormone, second messenger or other molecule. Anaerobic stress, for example, is due to a reduction in oxygen levels (hypoxia or anoxia) sufficient to produce a stress response. A flooding stress can be due to prolonged or transient immersion of a plant, plant part, tissue or isolated cell in a liquid medium such as occurs during monsoon, wet season, flash flooding or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Saline stress (salt stress) can be associated with or induced by a perturbation in the osmotic potential of the intracellular or extracellular environment of a cell. Osmotic stress also can be associated with or induced by a change, for example, in the concentration of molecules in the intracellular or extracellular environment of a plant cell, particularly where the molecules cannot be partitioned across the plant cell membrane.

An improvement in stress tolerance can be assessed by any quantitative or qualitative measure of plant performance under a given stress condition and is relative to the performance of a plant grown under the same stress conditions that has not been transformed with a nitrogen-modulating sequence of the invention. Thus, the plants may exhibit improved nitrogen contents, altered amino acid or protein compositions, altered carbohydrate composition, altered oil composition, vigorous growth characteristics, increased vegetative yields or better seed yields and qualities. These plants may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; 10) the total protein content of the fruit or seed; 11) measurable change in carbohydrates or oils. The procedures and methods for examining these parameters are well known to those skilled in the art. These methods may involve enzymatic assays and immunoassays to measure enzyme/protein levels; assays to measure the amino acid composition, free amino acid pool or total nitrogen content of various plant tissues; measurement of growth rates in terms of fresh weight gains over time; or measurement of plant yield in terms of total dry weight and/or total seed weight.

Transformation of Bacterial or Plant Cells

Provided herein are novel nucleotide sequences that modulate nitrogen utilization efficiency in plants. Also provided are amino acid sequences of the proteins of the invention, that may be nitrogen-modulating or modulated by nitrogen concentration.

The nitrogen-modulating nucleotide sequences of the invention may be modified to obtain or enhance expression in plant cells. The nitrogen-modulating sequences of the invention may be provided in expression cassettes for expression in the plant of interest. "Plant expression cassette" includes DNA constructs that are capable of resulting in the expression of a protein from an open reading frame in a plant cell. The cassette will include in the 5'-3' direction of transcription, a transcriptional initiation region (i.e., promoter) operably-linked to a DNA sequence of the invention, and a transcriptional and translational termination region (i.e., termination region) functional in plants. The cassette may additionally contain at least one additional gene to be co-transformed into the organism, such as a selectable marker gene or a stacked gene of different function. Alternatively, the additional gene(s) can be provided on multiple expression cassettes. Such an expression cassette is provided with a plurality of restriction sites for insertion of the nitrogen-modulating sequence to be under the transcriptional regulation of the regulatory regions.

By "promoter" is intended a nucleic acid sequence that functions to direct transcription of a downstream coding sequence. The promoter, together with other transcriptional and translational regulatory nucleic acid sequences (also termed as "control sequences"), are necessary for the expression of a DNA sequence of interest. Preferably, the promoter is one that is known to stimulate transcription in the organism into which the nucleotide sequence of the invention is being introduced.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, "operably linked" means that the nucleic acid sequences being linked are contiguous, including exons and introns and, where necessary to join two protein coding regions, contiguous and in the same reading frame.

In one embodiment, the promoter is a constitutive promoter. Suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689), including the TrpPro5 promoter (U.S. patent application Ser. No. 10/377,318; filed Mar. 16, 2005); pEMU (Last et al. (1991) *Theor. Appl. Genet.* 81:581-588); MAS (Velten et al. (1984) *EMBO J.* 3:2723-2730); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO 97/41228); and promoters of various *Agrobacterium* genes (see U.S. Pat. Nos. 4,771,002; 5,102,796; 5,182,200; and 5,428,147).

In another embodiment, the promoter is a tissue-specific promoter. A list of commonly-used tissue-specific promoters can be found in Reviewed in Moore et al. (2006) *Plant J.* 45(4):651-683, which is herein incorporated by reference in its entirety.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in co-translational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the nitrogen-modulating sequence of the present invention, or may be derived from another source. Convenient termination regions are available from the Ti-plasmid of *A. tumefaciens*, such as the octopine synthase and nopaline synthase termination regions, or the potato proteinase inhibitor II sequence (PinII) as described in Liu et al. (2004) *Acta Biochim Biophys Sin* 36(8):553-558. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "nucleotide sequence of interest" (a nucleotide sequence engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.
Altered or Improved Variants Useful in the Constructs of the Invention It is recognized that nucleotide and amino acid sequences useful in the present invention may be altered by various methods, and that these alterations may result in sequences encoding proteins with amino acid sequences different than that encoded by the nitrogen-modulating sequences disclosed herein.

Nucleotide sequences useful in the present invention include the sequences set forth in SEQ ID NO: 1, and variants, fragments, and complements thereof. As used herein, the term "nucleotide sequence" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecules can be single-stranded or double-stranded, but preferably are double-stranded DNA. By "complement" is intended a nucleotide sequence that is sufficiently complementary to a given nucleotide sequence such that it can hybridize to the given nucleotide sequence to thereby form a stable duplex. The corresponding amino acid sequences for the nitrogen-modulating proteins encoded by these nucleotide sequences are set forth in SEQ ID NO: 2, as well as variants and fragments thereof. The invention also encompasses the use of nucleic acid molecules comprising nucleotide sequences encoding partial-length nitrogen-modulating proteins, and complements thereof.

Nucleic acid molecules that are fragments of these nitrogen-modulating nucleotide sequences are also useful in the present invention. By "fragment" is intended a portion of a nucleotide sequence encoding a nitrogen-modulating protein. A fragment of a nucleotide sequence may encode a biologically active portion of a nitrogen-modulating protein, or it may be a fragment that can be used as a hybridization probe or PCR primer using methods disclosed below. Nucleic acid molecules that are fragments of a nitrogen-modulating nucleotide sequence comprise at least about 15, 20, 50, 75, 100, 200, 300, 350, or at least about 400 contiguous nucleotides, or up to the number of nucleotides present in a full-length nitrogen-modulating nucleotide sequence disclosed herein depending upon the intended use. By "contiguous" nucleotides is intended nucleotide residues that are immediately adjacent to one another.

Polypeptides that are fragments of these nitrogen-modulating polypeptides are also useful in the present invention. By "fragment" is intended a portion of an amino acid sequence encoding a nitrogen-modulating protein as set forth SEQ ID NO: 2, and that retains nitrogen utilization efficiency. A biologically active portion of a nitrogen-modulating protein can be a polypeptide that is, for example, 10, 25, 50, 100, 125, 150, 175, 200, 250, 300, 350, 400 or more amino acids in length. Such biologically active portions can be prepared by recombinant techniques and evaluated for nitrogen utilization efficiency. As used here, a fragment comprises at least 8 contiguous amino acids of SEQ ID NO: 2. The invention encompasses other fragments, however, such as any fragment in the protein greater than about 10, 20, 30, 50, 100, 150, 200, 250, 300, 350, or 400 amino acids.

The invention also encompasses the use of variant nucleic acid molecules, or variant amino acid sequences, in the methods and compositions of the inventions. "Variants" of the nitrogen-modulating nucleotide sequences include those sequences that encode a nitrogen-modulating protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the nitrogen-modulating proteins disclosed in the present invention as discussed below. Variant proteins useful in the present invention are biologically active, that is they retain the desired biological activity of the native protein, that is, nitrogen utilization efficiency and/or improved stress tolerance.

By "variants" is intended proteins or polypeptides having an amino acid sequence that is at least about 60%, 65%, about 70%, 75%, 80%, 85%, or 90%, 91%, 92%, 93%, 94%, 95%, 96%, 97%, 98% or 99% identical to the amino acid sequence of SEQ ID NO: 2. Variants also include polypeptides encoded by a nucleic acid molecule that hybridizes to the nucleic acid molecule of SEQ ID NO: 1, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retain nitrogen utilization efficiency and/or improved stress tolerance.

Preferred nitrogen-modulating proteins useful in the present invention are encoded by a nucleotide sequence sufficiently identical to the nucleotide sequence of SEQ ID NO: 1. The term "sufficiently identical" is intended an amino acid or nucleotide sequence that has at least about 60% or 65% sequence identity, about 70% or 75% sequence identity, about 80% or 85% sequence identity, or about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to nitrogen-modulating nucleic acid molecules of the invention. BLAST protein searches can be performed with the BLASTX program, score=50, wordlength=3, to obtain amino acid sequences homologous to nitrogen-modulating protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www(DOT)ncbi(DOT)nlm (DOT)nih(DOT)gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

A preferred program is GAP version 10, which used the algorithm of Needleman and Wunsch (1970) *J. Mol. Biol.* 48:443-453. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The skilled artisan will further appreciate that changes can be introduced by mutation into the nucleotide sequences of the invention thereby leading to changes in the amino acid sequence of the encoded nitrogen-modulating protein, without altering the biological activity of the protein. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, preferably nonessential amino acid residues. A "nonessential" amino acid residue is a residue that can be altered from the wild-type sequence of a nitrogen-modulating protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues. Examples of residues that are conserved and that may be essential for protein activity include, for example, residues that are identical between all proteins contained in an alignment of similar or related sequences known to be involved in nitrogen assimilation. Examples of residues that are conserved but that may allow conservative amino acid substitutions and still retain activity include, for example, residues that have only conservative substitutions between all proteins contained in an alignment of similar or related sequences known to be involved in nitrogen assimilation.

Alternatively, variant nucleotide sequences can be made by introducing mutations randomly along all or part of the coding sequence, such as by saturation mutagenesis, and the resultant mutants can be screened for ability to confer nitrogen utilization efficiency to identify mutants that retain activity. Following mutagenesis, the encoded protein can be expressed recombinantly, and the activity of the protein can be determined using standard assay techniques.

Using methods such as PCR, hybridization, and the like, corresponding nitrogen-modulating sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY). In a hybridization method, all or part of the nitrogen-modulating nucleotide sequence can be used to screen cDNA or genomic libraries. Methods for construction of such cDNA and genomic libraries are generally known in the art and are disclosed in Sambrook and Russell, 2001, supra.

Variants and fragments of the nucleotide or amino acid sequences of the present invention generally will encode protein fragments that retain the biological activity of the full-length nitrogen-modulating protein; i.e., retain nitrogen utilization efficiency. By "retains nitrogen utilization efficiency" is intended that the variant or fragment will have at least about 30%, at least about 50%, at least about 70%, or at least about 80% of the nitrogen utilization efficiency and/or stress tolerance of the full-length nitrogen-modulating protein disclosed herein as SEQ ID NO: 2, or the full-length nitrogen-modulating nucleotide sequence disclosed herein as SEQ ID NO: 1. Methods for monitoring nitrogen utilization efficiency include detecting a change in any of the main nitrogen metabolic pool sizes in the assimilation pathways (for example, a measurable change in nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content) or detecting the ability of a plant to provide the same or elevated yield at lower nitrogen fertilization levels, or the ability of a plant to provide elevated yields at the same nitrogen fertilization levels when compared to a plant that does not contain or express a nitrogen-modulating sequence of the invention. The designation of "same" or "lower" nitrogen fertilization levels refers to the level of nitrogen generally applied to a plant not expressing a nitrogen-modulating sequence of the invention. Sufficient nitrogen levels are known in the art for the majority, if not all, plant varieties of interest. Additional guidance may be found in, for example, Hewitt (1966) *Sand and Water Culture Methods Used in the Study of Plant Nutrition*, 2nd ed., Farnham Royal (Bucks), Commonwealth Agricultural Bureaux; and, Hewitt (1975) *Plant Mineral Nutrition*, London, English University Press.

The polypeptide sequences useful in the present invention may be altered in various ways including amino acid substitutions, deletions, truncations, and insertions. Methods for such manipulations are generally known in the art. For example, amino acid sequence variants of the nitrogen-modulating proteins disclosed herein can be prepared by mutations in the nucleotide sequences. This may also be accomplished by one of several forms of mutagenesis and/or in directed evolution. In some aspects, the changes encoded in the amino acid sequence will not substantially affect function of the protein. Such variants will possess the desired nitrogen utilization efficiency. However, it is understood that the ability of the nitrogen-modulating sequences of the invention to alter or improve nitrogen utilization may be further improved by one use of such techniques upon the compositions of this invention. For example, one may express the nucleotide sequences disclosed herein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), transform it into plants as described elsewhere herein, and measure nitrogen utilization efficiency.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different nitrogen-modulating protein coding regions can be used to create a new nitrogen-modulating protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the nitrogen-modulating sequence useful in the present invention and other known nitrogen-modulating sequences to obtain a new sequence coding for a protein with an improved property of interest, such as improved nitrogen utilization. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Plant Transformation

Methods of the invention involve introducing one or more nitrogen-modulating nucleotide sequences into a plant. In some embodiments, only one of the nitrogen-modulating sequences disclosed herein is introduced into the plant. In other embodiments, at least 2, at least 3, at least 4, or more of the sequences are introduced. Where multiple sequences are introduced, each of the nucleotide sequences is non-identical. Two nucleotide sequences are considered non-identical if they differ in at least one nucleotide position. Thus, non-identical nucleotide sequences include two or more different nucleotide sequences that each encodes the same amino acid sequence (e.g., one or more has been optimized for expression in the plant), as well as two or more different nucleotide sequences that encode at least two different amino acid sequences.

By "introducing" it is intended to present to the plant one or more constructs comprising the one or more nitrogen-modulating sequences in such a manner that the construct(s) gain(s) access to the interior of a cell of the plant. The methods of the invention do not require that a particular method for introducing a nucleotide construct to a plant is used, only that the nucleotide construct(s) gain(s) access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (i.e., antibiotics, such as spectinomycin and kanamycin). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can then be used to confirm the presence of the integrated heterologous gene of interest in the genome of transgenic plant.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Transformation of bacterial cells is accomplished by one of several techniques known in the art, including but not limited to electroporation or chemical transformation (see, for example, Ausubel, ed. (1994) *Current Protocols in Molecular Biology*, John Wiley and Sons, Inc., Indianapolis, Ind.). Markers conferring resistance to toxic substances are useful in identifying transformed cells (having taken up and expressed the test DNA) from non-transformed cells (those not containing or not expressing the test DNA).

In one aspect of the invention, the nucleotide sequences of the invention are useful as markers to assess transformation of bacterial or plant cells. In this manner, transformation is assessed by monitoring nitrogen utilization efficiency as described above.

Transformation of plant cells can be accomplished in similar fashion. By "plant" is intended whole plants, or component parts including plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Methods to Increase Plant Yield by Modulating Nitrogen Utilization

Methods for increasing plant yield are provided. The methods comprise introducing into a plant or plant cell a nitrogen-modulating nucleotide sequence disclosed herein such that an increase in nitrogen utilization efficiency corresponds to an increase in plant yield. As defined herein, the "yield" of the plant refers to the quality and/or quantity of biomass, and/or harvestable yield, produced by the plant. By "biomass" is intended any measured plant product (e.g., any component part of a plant, such as seed, stalk, root, grain, leaf, etc.). An increase in biomass production is any improvement in the yield of the measured plant product. An increase in harvestable yield is a higher weight of a plant component that is easily collected using known harvest methods, or an increase in the compositional amount of a compound of interest in the harvested part: a nonlimiting example, being the amount of an amino acid, such as lysine, that is harvested per unit land area. Increasing plant yield or harvestable yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in plant yield compared to the yield of a plant into which a nucleotide sequence that modulates use of nitrogen of the invention has not been introduced.
Plants The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, grasses (such as turf grasses, forage grasses, or pasture grasses), ornamentals, trees (such as fruit trees, nut trees, pulp trees, oil palms) and conifers.

Vegetables include, but are not limited to, onions, tomatoes, lettuce, green beans, lima beans, peas, and members of the genus *Curcumis* such as cucumber, cantaloupe, and muskmelon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated nucleotide sequences at the earlier stage before transplanting into the soil (Sambrook and Russell (2001) *Molecular Cloning: A Laboratory Manual*, Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragments to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by the nucleotide sequence of the invention is then tested by hybridizing the filter to a radioactive probe derived from a polynucleotide of the invention, by methods known in the art (Sambrook and Russell, 2001, supra)

Western blot and biochemical assays and the like may be carried out on the transgenic plants to determine the presence of protein encoded by the nitrogen-modulating gene by standard procedures (Sambrook and Russell, 2001, supra) using antibodies that bind to one or more epitopes present on the nitrogen-modulating protein. For example, the polyclonal antibodies generated by the methods of the present invention can be used to detect the presence of a nitrogen-modulating protein.

Antibodies

Antibodies to the polypeptides useful in the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

EXPERIMENTAL

Materials and Methods

A synthetic gene encoding an NAGK enzyme was generated (SEQ ID NO: 1). In order to localize the NAGK protein in the chloroplast, a polynucleotide encoding a chloroplast transit peptide (SEQ ID NO: 3) was added to the N-terminus of the protein.

Functional Characterization of NAGK Protein

An argB (encodes NAGK in *E. coli*) deletion strain was constructed from *E. coli* DH5 alpha using the method described by K. A. Datsenko and B. L. Wanner (One-step inactivation of chromosomal genes in *Escherichia* coli K-12 using PCR products. PNAS 97(12):6640-6645. 2001.) The PCR primers described by Baba, et al. (T. Baba, T. Ara, M. Hasegawa, Y. Takai, Y. Okumura, M. Baba, K. A. Datsenko, M. Tomita, B. L. Wanner & H. Mori. 2006. Construction of *Escherichia coli* K-12 in-frame, single-gene knockout mutants: the Keio collection Molecular Systems Biology 2:2006.0008) were used to create an in-frame deletion of the argB gene. Mutants were selected on kanamycin and the kanamycin resistance cassette subsequently was removed by FLP recombinase.

This deletion strain was named DH5 alpha ΔargB. A DNA fragment spanning the deletion was amplified by PCR and the PCR product was sequenced, confirming the structure of the deletion. This strain grew normally on rich media (e.g., LB, TB) but was unable to grow on M63 minimal medium unless the medium was supplemented with arginine or ornithine, as was expected for a strain lacking a functional NAGK enzyme. We generated a synthetic gene encoding NAGK to simplify the cloning steps and improve the expression of the NAGK protein in maize. Additionally, we directed localization of the NAGK enzyme to the plant chloroplast using the chloroplast transit peptide (CTP) from the 5' end of the enolpyruvyl shikimate phosphate synthase (EPSPS) gene from the algae *Chlamydomonas reinhardtii*. Various plasmids containing the synthetic gene, the cosmid containing the NAGK gene from parent bacterial strain ATX 16042 and a negative control plasmid containing a maize glutamine synthetase gene were transformed into *E. coli* strain DH5 alpha ΔargB. The presence and identity of the plasmids was confirmed by DNA miniprep and restriction digest. The plasmid-containing strains were streaked onto M63 agar medium and onto M63 supplemented with ornithine or arginine. The cultures were incubated at 37° C. for 2 days and growth was evaluated. Results are shown in Table 1 below.

TABLE 1

Functional Characterization of the NAGK gene

| | | Growth on | | |
|---|---|---|---|---|
| Plasmid | Description | M63 | M63 + orn | M63 + arg |
| pAXX4371 | Cosmid clone encoding NAGK from strain ATX16042 | ++ | ++ | ++ |
| pAXX4381 | pRSF1b vector containing maize glutamine synthetase gene | − | ++ | ++ |
| pAXX4383 | pGA4 vector containing synthetic NAGK gene | + | ++ | ++ |
| pAXX4389 | pRSF1b vector containing synthetic NAGK gene | ++ | ++ | ++ |
| pAXX4395 | Plant transformation vector containing synthetic CTP-NAGK gene | ++ | ++ | ++ |

Protein Overexpression in Maize

The plant transformation vector pAX4395 was constructed to direct overexpression of the NAGK protein in maize. The vector utilizes the Scubi4 promoter and PinII terminator to guide overexpression of a protein comprising a *Chlamydomonas* EPSPS chloroplast leader fused to NAGK. A second cassette in the vector guides the overexpression of the dsdA1 gene, leading to accumulation of the d-amino acid oxidase protein. Each of the gene cassettes was sequenced completely prior to plant transformation.

Plant Transformation

The pAX4395 vector was used to carry out *Agrobacterium*-mediated transformation of maize. Following vector construction and transformation of *Agrobacterium*, the vectors were confirmed by Southern blot by methods known in the art. Positive *Agrobacterium* strains that passed these tests were then grown on a solid medium to produce cell counts for large-scale transformation experiments.

The vector pAX4395 was introduced into an *Agrobacterium tumefaciens* strain by electroporation. This strain also contained the vector pSB1, which allows pSB1 and pAX4395 to recombine in vivo to create a vector that can direct insertion of the NAGK cassette into the maize genome. The formation of the recombinant vector, pAG4395, was confirmed by Southern blot hybridization of this *Agrobacterium* strain.

The *Agrobacterium* strain harboring the cointegrate can be used to transform plants, for example, by the PureIntro method (Japan Tobacco, Inc.). Following co-cultivation, the embryos were grown on selection medium containing d-serine to identify callus that had integrated the dsdA gene from pAG4395 and expressed the d-amino acid oxidase protein. Individual events that survived selective growth in the presence of serine were then moved to regeneration medium and grown to the plantlet stage using methods known in the art.

Western Blot Analysis

Expression of NAGK in these plants was examined by generating antibodies that bind specifically to the NAGK protein. Briefly, the NAGK gene was subcloned into the vector pRSF1b (Novagen) to allow overexpression of the NAGK protein in *E. coli* following IPTG induction. The vector also introduces a 6× His tag at the N-terminus of the protein. Following protein overexpression, the NAGK protein was purified by cobalt column chromatography and the identity of the purified protein was confirmed by N-terminal sequencing. The purified protein was then used to immunize rabbits, with serum collection beginning 42 days after immunization.

Next, the NAGK antiserum was used to assess protein expression in the transgenic maize plants by Western blot analysis. Leaf samples were taken from individual plants following 4 weeks of growth in the greenhouse, and protein extracts were prepared by grinding the plant material in water. Protein concentration in each extract was determined by Bradford assay, and 25 ug of each extract was separated on polyacrylamide gels with a 4-12% gradient. The separated proteins were transferred to nitrocellulose and then probed with the rabbit antiserum at a 1:5000 dilution. Following wash steps, the nitrocellulose was contacted with goat anti-rabbit conjugated with horseradish peroxidase (1:10,000 dilution), and antibody complexes were visualized using ECL detection reagents (GE Healthcare). Four representative transgenic events (#8054, 8055, 8056, 8057) each show strong expression of the NAGK protein, while a control plant ("Hi-II") did not show the presence of the protein. It is important to note that the size of the protein detected in plant tissue (~29 kDa) is consistent with the size of the NAGK after processing of the chloroplast leader (predicted size=29.2 kDa) rather than the unprocessed chloroplast leader-NAGK fusion protein (predicted size=36.9 kDa).

Maize Nitrogen Analysis

A series of assays that quantify nitrogen intermediates in plants have been developed. These nitrogen assay methods are described in a previous patent filing (WO 2008/051608 "Plants with improved nitrogen utilization and stress tolerance"). These assays were utilized here to analyze a total of 10 transgenic plants containing the NAGK gene. Each of the plants was sampled (leaf) following 4 weeks of growth in soil in a greenhouse. These leaf samples were processed to determine their nitrate, asparagine, glutamine, aspartic acid, glutamic acid, ammonium, total amino acid, chlorophyll, and total protein levels. Included alongside in the analysis were plants that were transformed with a construct containing only the dsdA1 selectable marker (no NAGK). These plants were likewise sampled at 4 weeks and are referred to as "non-GOI" plants. The results of the nitrogen assays carried out on both types of plants are shown below in Table 2.

TABLE 2

Nitrogen levels, NAGK vs. non-GOI maize events, 4 weeks after transfer to soil

| Plant# | GOI | Nitrate (ug/g) | Asparagine (ug/g) | Glutamine (ug/g) | Aspartic Acid (ug/g) | Glutamic Acid (ug/g) | Ammonium (ug/g) | Total Amino Acids (mg/g) | Total Protein (mg/g) | Total Chlorophyll a + b (mg/g) |
|---|---|---|---|---|---|---|---|---|---|---|
| 8054 | NAGK | 275 | 90 | 333 | 251 | 1875 | 289 | 173 | 9.5 | 0.070 |
| 8055 | NAGK | 782 | 73 | 287 | 298 | 2197 | 368 | 159 | 9.4 | 0.084 |
| 8056 | NAGK | 239 | 916 | 250 | 243 | 1765 | 355 | 174 | 11.1 | 0.138 |
| 8057 | NAGK | 437 | 240 | 319 | 630 | 3347 | 236 | 183 | 14.5 | 0.080 |
| 8570 | NAGK | 438 | 276 | 430 | 588 | 2170 | 229 | 169 | 10.6 | 0.077 |

TABLE 2-continued

Nitrogen levels, NAGK vs. non-GOI maize events, 4 weeks after transfer to soil

| Plant# | GOI | Nitrate (ug/g) | Asparagine (ug/g) | Glutamine (ug/g) | Aspartic Acid (ug/g) | Glutamic Acid (ug/g) | Ammonium (ug/g) | Total Amino Acids (mg/g) | Total Protein (mg/g) | Total Chlorophyll a + b (mg/g) |
|---|---|---|---|---|---|---|---|---|---|---|
| 8571 | NAGK | 373 | 237 | 516 | 418 | 2128 | 254 | 163 | 12.5 | 0.049 |
| 8572 | NAGK | — | 62 | 289 | 695 | 2640 | 183 | 143 | 9.8 | 0.069 |
| 8573 | NAGK | 363 | 177 | 434 | 704 | 2143 | 262 | 152 | 10.9 | 0.046 |
| 8643 | NAGK | 291 | 45 | 366 | 621 | 2123 | 132 | 122 | 10.9 | 0.031 |
| 8644 | NAGK | 694 | 55 | 218 | — | 2220 | 152 | 117 | 11.2 | 0.029 |
| Avg | | 432 | 217 | 344 | 494 | 2281 | 246 | 155 | 11.0 | 0061 |
| StdDev | | 188 | 261 | 93 | 192 | 445 | 78 | 22 | 1.5 | 0.032 |
| CV | | 0.43 | 1.20 | 0.27 | 0.39 | 0.20 | 0.32 | 0.14 | 0.14 | 0.47 |
| 8058 | non-GOI | 362 | 89 | 234 | 452 | 2540 | 201 | 115 | 8.04 | 0.053 |
| 8059 | non-GOI | 219 | 82 | 222 | 287 | 1687 | 227 | 122 | 11.41 | 0.081 |
| 8060 | non-GOI | 751 | 80 | 225 | 312 | 2083 | 276 | 142 | 10.58 | 0.099 |
| Avg | | 444 | 84 | 227 | 351 | 2103 | 235 | 121 | 10.01 | 0.078 |
| StdDev | | 275 | 5 | 6 | 89 | 427 | 38 | 14 | 1.76 | 0.023 |
| CV | | 0.62 | 0.06 | 0.03 | 0.25 | 0.20 | 0.16 | 0.11 | 0.18 | 0.30 |

These data demonstrate that the synthetic gene we designed encodes a functional NAGK enzyme.

Construction of NAGK Overexpression Vector

The following NAGK DNA sequence (SEQ ID NO:1) was isolated from a *Brevibacillus laterosporus* bacterial isolate:

ATGCTGCATGAGGTGATGGTGATCAAGTGCGGCGGCAGCATGCTGGAGCA

GCTGCCGGAGAGCTTCTACAACAAGCTGGCGACGCTGCAAGCAGAAGGAA

GAAGCATCGTCATTGTTCATGGAGGAGGGCCGGCCATCAACCAGATGCTG

GAGCAGCTGAAGATTGAGCCAACCTTCTCAAATGGGCTGAGGGTGACAGA

TGAGCCAACAATGCAAGCTGTGGAGATGGTGCTCTCAGGGCCCATCAACA

AGCTGGTGGTGAGGAAGCTGCTGCACGCCGGCGGCAAGGCATGGGGCCTC

AGCGGCGTGGATGGAAGCCTGCTGCAAGCTGTTGAGAAGACTCAAGGCCT

CGGCCTGGTGGGCAGCATCACCGTGGTGGATCAAGCGCCGCTCCAGCTGC

TGCTGAGCAATGGCTACATCCCGGTGGTGTCTCCCATCGCCGTCTCAGAA

GATGGAAGAACAAGATACAACTGCAACGCCGACACCGTCGCCGGCGCCAT

TGCTTCAGCTCTCGGCGCCAAGCAGCTGCTGATGCTCACTGATGTTCCTG

GCATCTGGGCAGAAAATGAGCTGGGAGAGAAGCAGCTGCTGCCGACGGTG

ACAACAGAAGATATTCAGCTGATGATGAAGAACCAGATCATCACCGGCGG

CATGATCCCCAAGGTGCAAGCGGCGCTGGATGCTCTAGCTCAAGGAGTTC

AAGAAGTGGTGATCTGCAAAGGAGAAGCTGAGACGCTGGACGGCGTGGTG

AAGGGCATGGCCGTCGGCACCTCCATCTCCGCCGAGATGAGCAGAGGACA

AGATTCTCAAGCCTTCATCAGCAACAAGGTGTGAGG

The NAGK DNA sequence shown above encodes the following NAGK protein sequence (SEQ ID NO:2):

MLHEVMVIKC GGSMLEQLPE SFYNKLATLQ AEGRSIVIVH

GGGPAINQML EQLKIEPTFS NGLRVTDEPT MQAVEMVLSG

PINKLVVRKL LHAGGKAWGL SGVDGSLLQA VEKTQGLGLV

GSITVVDQAP LQLLLSNGYI PVVSPIAVSE DGRTRYNCNA

DTVAGAIASA LGAKQLLMLT DVPGIWAENE LGEKQLLPTV

TTEDIQLMMK NQIITGGMIP KVQAALDALA QGVQEVVICK

GEAETLDGVV KGMAVGTSIS AEMSRGQDSQ AFISNKV

The DNA sequence was cloned into *E. coli* expression vector pRSF-1b (Novagen, Inc.) to create vector pAX4389. This expression vector placed a 6-histidine tag at the N-terminus of the protein, and places the expression of the NAGK gene under the control of the viral T7 promoter. The vector map for pAX4389 is shown in FIG. 1.

Preparation of NAGK Protein Extract

NAGK overexpression vector pAX4389 was transformed into electrocompetent *E. coli* cells (BL21 *DE3, Invitrogen) and single colonies were obtained by selection on the antibiotic kanamycin. An individual colony was then grown in liquid medium (LB broth) until the culture absorbance (at 600 nm) reached 0.6, and then 0.5 mM IPTG was added to induce expression from the T7 promoter. Induction was carried out overnight at 16° C. The following day, the induced culture was centrifuged and the pellet was frozen for two hours at −20° C. After thawing on ice, the pellet was resuspended in 1110th volume of lysis buffer (50 mM Hepes, pH 7.0, 50 mM NaCl), treated with Lysozyme (Novagen) at room temperature for 30 minutes, and then sonicated to lyse the cells. Insoluble material was separated from the soluble protein extract through centrifugation. This protein extract was then stored in an ice bucket, and NAGK enzyme assays were prepared a short time later. As a negative control, a control vector was prepared alongside that directed the overexpression of a bacterial EPSPS enzyme in the same base vector (pRSF-1b). This vector was likewise transformed into the same *E. coli* cell line and a transformant colony was selected for protein overexpression and a protein extract was prepared alongside NAGK.

NAGK Enzyme Assay—Titration with NAGK Enzyme

The NAGK enzyme assay was adapted from the method of Denes (1970). Product formation was quantified using a Spectramax 190 spectrophotometer at 540 nm.

A master mix for the NAGK in vitro reaction was prepared with the following components: 50 mM Tris, pH 8.0; final pH of the master mix was 5.5; 100 mM hydroxylamine (NH$_2$OH); 10 mM MgCl$_2$; 7 mM ATP; 70 mM N-acetylglutamate (NAG).

This master mix was subdivided into individual wells in a 96-well plate (200 uL/well final volume), and reactions were then initiated by adding various concentrations of NAGK protein extract into individual sample wells. Following 1 hour of incubation at 37° C., the absorbance of each sample was quantified. The quantity of NAGK protein in the extract was estimated by loading dilutions of the extract on a SDS-polyacrylamide gel alongside known concentrations of a bovine serum albumin standard, and then staining the gel with Coomassie protein stain (Simply Blue, Invitrogen).

By this method, it was observed that addition of NAGK protein extract at concentrations as low as 1 ng/mL generated an absorbance product at 540 nm. The absorbance results from the enzyme product (N-actylglutamyl-5-phosphate) reacting with hydroxylamine to create the absorbent compound N-acetyglutamyl-5-hydroxamate. The graph (FIG. 1) and table (Table 3) show the absorbance at each of 6 different concentrations of NAGK protein. The baseline absorbance generated by a buffer control (A540=0.04) was subtracted from each NAGK absorbance value. The absorbance generated by a high concentration of the control extract (bacterial EPSPS) was very similar to the buffer control (A540=0.042), which demonstrates that product formation requires the presence of the NAGK enzyme.

TABLE 3

Primary absorbance data for NAGK in vitro enzyme assay shown in FIG. 1. The absorbance value for the buffer control (A540 = 0.040) has been subtracted from each value.

| NAGK (ng/mL) | A540 nm |
|---|---|
| 1000 | 0.872 |
| 250 | 0.518 |
| 62.5 | 0.0159 |
| 15.6 | 0.039 |
| 3.9 | 0.002 |
| 1 | 0.001 |

NAGK Enzyme Assay—Titration with Substrate (NAG)

The following master mix for NAGK in vitro enzyme assays was prepared for the purpose of titrating the substrate (NAG) into the reaction: 50 mM Tris; final pH was 5.5; 100 mM hydroxylamine (NH$_2$OH); 10 mM MgCl$_2$; 7 mM ATP; 1000 ng/mL NAGK enzyme (from protein extract).

This master mix was subdivided into individual wells in a 96-well plate (200 uL/well final volume), and reactions were then initiated by adding various concentrations of the substrate NAG into individual sample wells. The NAG concentrations ranged from 1.6 mM up to 100 mM. Following 1 hour of incubation at 37° C., the absorbance of each sample was quantified. A control reaction without substrate was prepared an analyzed alongside.

By this method, it was observed that formation of product (by the NAGK enzyme) was substrate concentration dependent. At the lowest substrate concentrations tested (NAG=1.6 mM, 3.1 mM), the quantity of product generated was approximately proportional to the substrate concentration. At the highest substrate concentrations tested (NAGK=50 mM, 100 mM), the substrate was in excess and only slight differences in product formation were observed. A graph of these data is shown in FIG. 3, and the numerical absorbance values are shown in Table 4.

TABLE 4

Figure 3:
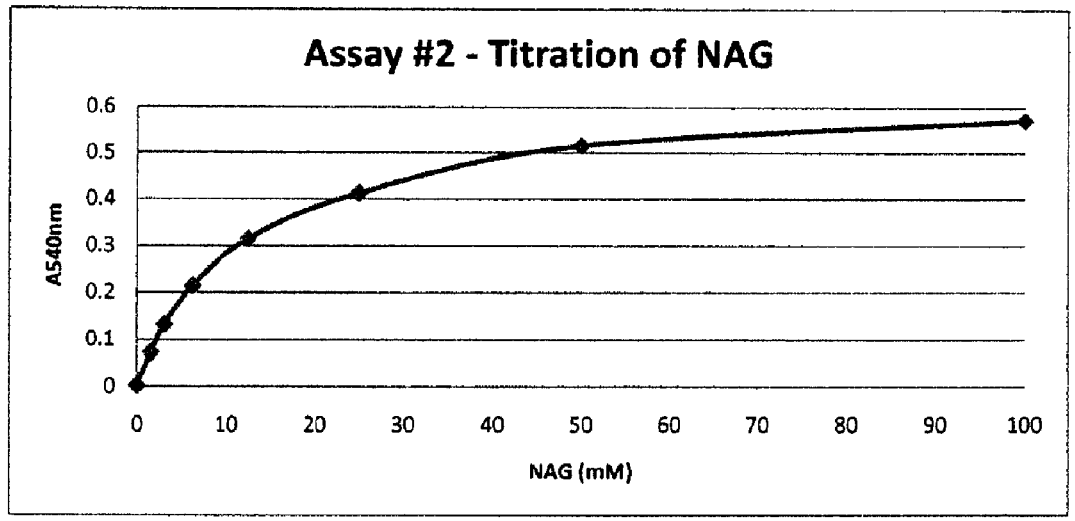
FIG. 3 is a graph of an NAGK in vitro enzyme assay; titration with substrate. Addition of NAGK enzyme to varying concentrations of substrate (NAG) leads to the formation of product in an substrate-dependent manner.

Primary absorbance data for NAGK in vitro enzyme assay shown in FIG. 3. The absorbance value for the control reaction without substrate (A540 = 0.041) has been subtracted from each value.

| NAG (mM) | A540 nm |
|---|---|
| 100 | 0.57 |
| 50 | 0.515 |
| 25 | 0.411 |
| 12.5 | 0.313 |
| 6.3 | 0.0212 |
| 3.1 | 0.13 |
| 1.6 | 0.07 |

NAGK Enzyme Assay—Titration with Arginine

The following master mix for NAGK in vitro enzyme assays was prepared for the purpose of determining the effect of arginine on NAGK enzyme activity: 50 mM Tris; final pH was 5.5; 100 mM hydroxylamine (NH$_2$OH); 10 mM MgCl$_2$; 7 mM ATP; 70 mM NAG.

This master mix was subdivided into individual wells in a 96-well plate (200 uL/well final volume), and then varying concentrations of arginine (0.15 mM to 10 mM) were then added to individual wells. The enzyme reactions were then initiated by addition of NAGK enzyme (100 ng/mL). Following 30 minutes of incubation at 37° C., the absorbance of each sample was quantified. A control reaction without arginine was prepared an analyzed alongside.

By this method, it was observed that formation of product (by the NAGK enzyme) was insensitive to the concentration of arginine over the range of concentrations tested. A graph of these data is shown in FIG. 4, and the numerical absorbance values are shown in Table 5.

TABLE 5

Figure 4:
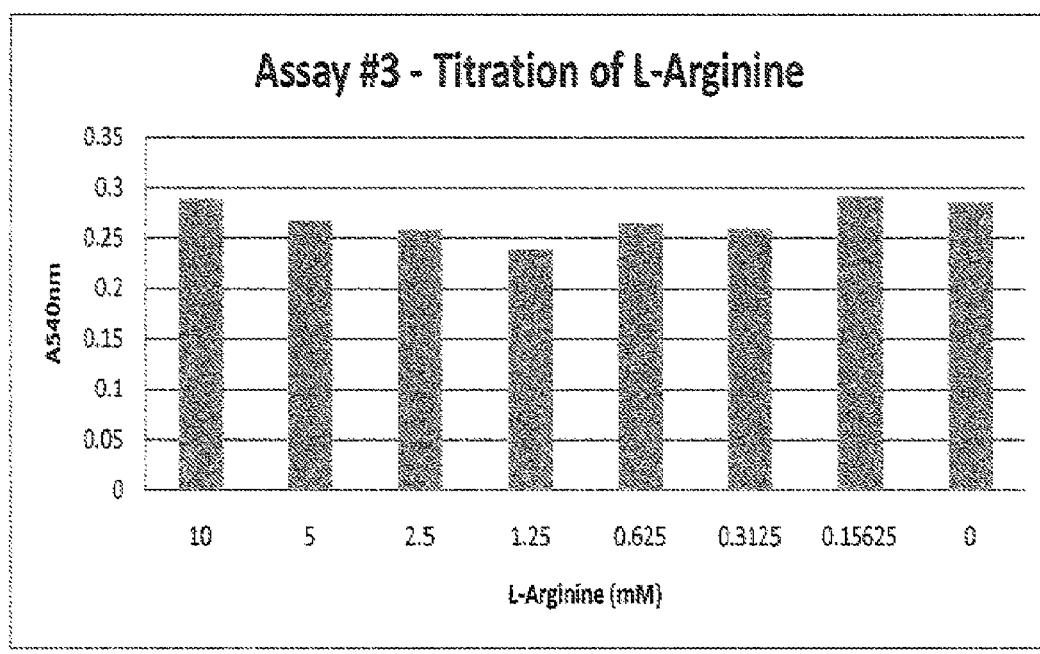
FIG. 4 is a graph of an NAGK in vitro enzyme assay; titration with arginine. Product formation by the NAGK enzyme was insensitive to the presence of arginine over the range of concentrations tested.

Primary absorbance data for NAGK in vitro enzyme assay shown in FIG. 4.

| Arginine (mM) | A540 nm |
|---|---|
| 10 | 0.287 |
| 5 | 0.266 |
| 2.5 | 0.257 |
| 1.25 | 0.237 |
| 0.63 | 0.263 |
| 0.31 | 0.259 |
| 0.16 | 0.291 |
| 0 | 0.284 |

Maize Plants Containing NAGK Gene Produce Increased Number of Grains per Plant

Seeds from a maize event containing the NAGK gene (#8057) were planted in an outdoor research site alongside negative segregant controls. A total of 5 plots (average of 55 plants per plot) were grown for both the transgenic and the control line. Typical field practices were used during growth of these plants, except that supplemental nitrogen was not applied prior to planting. At the end of the growing season, the total grain yield (adjusted to 15% grain moisture) was measured for all of the plants in each plot. Additionally, the average number of kernel rows per ear (10 plants per plot) and the average number of kernels per row (10 plants per plot) was recorded and the data are shown in Table 6.

TABLE 6

Grain Yield, Rows per Ear, Kernels per Row for NAGK Event 8057.

| Genotype | Grain Yield (Bushels/Acre @ 15% Moisture) (+/−Standard Deviation) | Rows per Ear (+/−Standard Deviation) | Kernels per Row (+/−Standard Deviation) |
|---|---|---|---|
| NAGK | 177.6 +/− 30.4 | 13.8 +/− 0.4 | 39.2 +/− 2.4 |
| Control | 143.2 +/− 19.3 | 13.3 +/− 0.1 | 33.8 +/− 1.7 |

Maize Plants Containing NAGK Gene Produce Increased Number of Ears per Plant

The ear from a T0 maize event containing the NAGK gene (#8644) was pollinated with an inbred line, and the T1 seeds were harvested. Next, 4 positive segregant T1 plants were grown under greenhouse conditions to maturity. The number of ears that were generated by each of the T1 plants was recorded and the data are shown in Table 7.

TABLE 7

Number of Ears per Plant for NAGK Event 8644.

| Genotype | Plant Number | Number of Ears on Plant |
|---|---|---|
| NAGK | T1 plant #1 | 2 |
| NAGK | T1 plant #2 | 3 |
| NAGK | T1 plant #3 | 3 |
| NAGK | T1 plant #4 | 3 |

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto. Those skilled in the art who have the disclosure before them will be able to make modifications and variations therein without departing from the scope of the invention.

We claim:

1. A plant, plant cell, plant material or seed of a plant which comprises an arginine insensitive N-acetyl glutamate kinase (NAGK) gene which encodes a protein having the amino acid sequence of SEQ ID NO: 2.

2. A plant that has been regenerated from a plant cell or seed according to claim 1, which comprises said NACK gene.

3. A method for improving plant yield, comprising the step of transforming the plant with at least an arginine-insensitive NAGK gene which encodes a protein having the amino acid sequence of SEQ ID NO: 2, wherein yield is increased compared to a plant not comprising said NAGK gene.

4. A plant transformed with a nucleotide sequence selected from the group consisting of:
   a) the nucleotide sequence SEQ ID NO: 1; and
   b) the nucleotide sequence encoding the amino acid sequence of SEQ ID NO: 2.

5. An expression vector comprising a nucleotide sequence selected from the group consisting of:
   a) the nucleotide sequence SEQ ID NO: 1; and
   b) a nucleotide sequence encoding the amino acid sequence of SEQ ID NO: 2.

6. An expression vector according to claim 5, further comprising a 5' DNA promoter sequence and a 3' terminator sequence, wherein the nucleotide sequence, the DNA promoter sequence, and the terminator sequence are operatively coupled to permit transcription of the nucleotide sequence.

7. An expression vector according to claim 6, wherein the promoter sequence is selected from the group consisting of constitutive plant promoters and tissue specific promoters.

8. A plant transformed with at least a first nucleotide sequence selected from the group consisting of:
   a) the nucleotide sequence of SEQ ID NO: 1; and
   b) a nucleotide sequence encoding the amino acid sequence of SEQ ID NO: 2.

9. A plant according to claim 8, wherein the plant is selected from the group consisting of corn (maize); sorghum; wheat; sunflower; tomato; crucifers; peppers; potato; cotton; rice; soybean; sugarbeet; sugarcane; tobacco; barley; and oilseed rape; Brassica sp.; alfalfa; rye; millet; safflower; peanuts; sweet potato; cassava; coffee; coconut; pineapple; cocoa; tea; banana; avocado; fig; guava; mango; olive; papaya; cashew; macadamia; almond; oats; vegetables; grasses; vegetables including onions, tomatoes, lettuce, green beans, lima beans, peas, members of the genus Curcumis including cucumber, cantaloupe, muskmelon; ornamentals including azalea, hydrangea, hibiscus, roses, tulips, daffodils, petunias, carnation, poinsettia, chrysanthemum; pulp trees; oil palm; and conifers.

10. A part of a plant of claim 9, which comprises a nucleotide sequence encoding SEQ ID NO: 2.

11. A plant seed produced from a plant of claim 9, which comprises a nucleotide sequence encoding SEQ ID NO: 2.

12. A plant seed transformed with a vector of claim 5.

13. A host cell transformed with at least a first nucleotide sequence selected from the group consisting of:
   a) the nucleotide sequence SEQ ID NO: 1; and
   b) a nucleotide sequence encoding the amino acid sequence of SEQ ID NO: 2.

14. The host cell of claim 13, wherein said host cell further comprises at least a second nucleotide sequence selected from (a) or (b), wherein said first and said second nucleotide sequences are non-identical.

15. A host cell according to claim 13, wherein the host cell is selected from the group consisting of bacterial cells and plant cells.

16. A vector, comprising:
   a) at least a first nucleotide sequence encoding an amino acid sequence selected from the group consisting of:
      i) the nucleotide sequence SEQ ID NO: 1;
      ii) a nucleotide sequence encoding the amino acid sequence of SEQ ID NO: 2;
   b) a 5' DNA promoter sequence; and
   c) a 3' terminator sequence, wherein the nucleotide sequence, the DNA promoter sequence, and the terminator sequence are operatively coupled to permit transcription of the nucleotide sequence.

17. A vector according to claim 16, further comprising at least a second nucleotide sequence encoding an amino acid sequence selected from (a)(i) or (a)(ii), wherein the amino acid sequences encoded by said first and said second nucleotide sequences are non-identical.

18. A method of expressing a nucleic acid molecule in a plant, said method comprising the steps of providing a transgenic plant or plant seed transformed with a vector according to claim 6, and growing the transgenic plant or a plant grown from the transgenic plant seed under conditions effective to express the nucleic acid molecule in said transgenic plant or said plant grown from the transgenic plant seed.

19. A method according to claim 18, wherein expression of the nucleic acid molecule results in increased yield in said transgenic plant or said plant grown from the transgenic plant seed when compared to a plant not comprising said vector.

20. A method according to claim 18, wherein the plant is selected from the group consisting of corn (maize); sorghum; wheat; sunflower; tomato; crucifers; peppers; potato; cotton; rice; soybean; sugarbeet; sugarcane; tobacco; barley; and oilseed rape; Brassica sp.; alfalfa; rye; millet; safflower; peanuts; sweet potato; cassava; coffee; coconut; pineapple; cocoa; tea; banana; avocado; fig; guava; mango; olive; papaya; cashew; macadamia; almond; oats; vegetables; grasses; vegetables including onions, tomatoes, lettuce, green beans, lima beans, peas, members of the genus Curcumis including cucumber, cantaloupe, muskmelon; ornamentals including azalea, hydrangea, hibiscus, roses, tulips, daffodils, petunias, carnation, poinsettia, chrysanthemum; pulp trees; oil palm; and conifers.

21. A transgenic plant according to claim 1, wherein the plant is corn and wherein the plant transformed with the NAGK gene of claim 1 has increased grain number compared to a corn plant not comprising said NAGK gene.

22. A transgenic corn plant as defined in claim 21, wherein the increased grain number is the result of either an increased average number of kernels per ear or an increased average number of ears per plant or both.

23. A method of improving the grain number of a corn plant compared to a control plant, comprising the steps of introducing into the genome of the plant the NAGK gene of claim 1 and growing the transformed plant to produce grain.

* * * * *

UNITED STATES PATENT AND TRADEMARK OFFICE
CERTIFICATE OF CORRECTION

| | | |
|---|---|---|
| PATENT NO. | : 8,692,070 B2 | Page 1 of 1 |
| APPLICATION NO. | : 12/916854 | |
| DATED | : April 8, 2014 | |
| INVENTOR(S) | : McLaren et al. | |

It is certified that error appears in the above-identified patent and that said Letters Patent is hereby corrected as shown below:

In the Claims

Column 29, line 7 (Claim 2, line 2) the term "NACK" is used instead of the correct term "NAGK".

Signed and Sealed this
Seventeenth Day of June, 2014

Michelle K. Lee
*Deputy Director of the United States Patent and Trademark Office*